(12) United States Patent
Pichler

(10) Patent No.: US 11,866,684 B2
(45) Date of Patent: Jan. 9, 2024

(54) DEVICE AND METHOD FOR MICRO-PET OR MICRO-SPECT OF A CELL CULTURE

(71) Applicant: DOC MEDIKUS GMBH, Krems (AT)

(72) Inventor: Verena Pichler, Vienna (AT)

(73) Assignee: DOC MEDIKUS GMBH, Krems (AT)

( * ) Notice: Subject to any disclaimer, the term of this patent is extended or adjusted under 35 U.S.C. 154(b) by 751 days.

(21) Appl. No.: 17/041,632

(22) PCT Filed: Mar. 26, 2019

(86) PCT No.: PCT/EP2019/057479
§ 371 (c)(1),
(2) Date: Sep. 25, 2020

(87) PCT Pub. No.: WO2019/185565
PCT Pub. Date: Oct. 3, 2019

(65) Prior Publication Data
US 2021/0047601 A1 Feb. 18, 2021

(30) Foreign Application Priority Data
Mar. 26, 2018 (EP) .................................... 18163900

(51) Int. Cl.
*C12M 1/00* (2006.01)
*G01T 1/164* (2006.01)
*C12M 1/34* (2006.01)
*G01T 1/29* (2006.01)

(52) U.S. Cl.
CPC ............ *C12M 29/10* (2013.01); *C12M 29/04* (2013.01); *C12M 41/16* (2013.01); *G01T 1/1642* (2013.01); *G01T 1/2985* (2013.01)

(58) Field of Classification Search
CPC ...... C12M 29/10; C12M 29/04; C12M 41/16; C12M 41/46; G01T 1/1642; G01T 1/2985
See application file for complete search history.

(56) References Cited

U.S. PATENT DOCUMENTS

2017/0198246 A1 7/2017 Niazi

FOREIGN PATENT DOCUMENTS

| WO | WO 89/10397 A1 | 11/1989 |
| WO | 2015/060979 A1 | 4/2015 |

OTHER PUBLICATIONS

Search Report and Written Opinion received for Singapore Application No. 11202009282X, completed Apr. 6, 2022.
(Continued)

*Primary Examiner* — Courtney D Thomas
(74) *Attorney, Agent, or Firm* — Greer, Burns & Crain, Ltd

(57) ABSTRACT

A biocompatible column for concurrent micro-positron emission tomography (micro-PET) or micro-single photon emission computed tomography (micro-SPECT) of at least two cell cultures is provided, the column having an inlet, an axially oriented perfusion chamber and an outlet, wherein the perfusion chamber includes a porous solid phase with sponges having biopolymer (such as silk, silk fibroin, collagen, gelatin, agarose, alginate, polylactic acid, agar, or methyl-cellulose), an aqueous liquid phase, a first cell culture and a second cell culture, wherein the first cell culture and the second cell culture are in contact with the solid phase and wherein the first cell culture is separated from the second cell culture by the solid phase. Also provided is a method and a kit for concurrent micro-PET or micro-SPECT of at least two cell cultures.

15 Claims, 5 Drawing Sheets

(56) References Cited

OTHER PUBLICATIONS

Office Action dated dated Jan. 13, 2023 for Japanese Application No. 2021-501085.
European Search Report from European Patent Application No. 18163900.6 dated Nov. 30, 2018.
International Search Report and Written Opinion for International Patent Application No. PCT/EP2019/057479, dated Aug. 12, 2019.
Carfi-Pavia, F. et al,. "Porous poly (L-lactic acid) scaffolds are optimal substrates for internal colonization by A6 mesoangioblasts and immunocytochemical analyses," J. Biosci. 34, (2009), pp. 873-879.
Chatziioannou, A., "Instrumentation for molecular imaging in preclinical research: Micro-PET and Micro-SPECT," Proceedings of the American Thoracic Society 2.6, (2005), pp. 533-536.
Hirschhaeuser, F., et al., "Multicellular tumor spheroids: an underestimated tool is catching up again," Journal of Biotechnology 148, No. 1, (2010), 13 pages.
Keshari, K., et al., "Metabolic response of prostate cancer to nicotinamide phophoribosyltransferase inhibition in a hyperpolarized MR/PET compatible bioreactor," The Prostate 75, No. 14, (2015), pp. 1601-1609.
Koba, W., et al., "MicroPET/SPECT/CT Imaging of Small Animal Models of Disease," The American Journal of Pathology 182, No. 2, (2013), pp. 319-324.
Mizuno, S., et al., "Effects of physical stimulation on chondrogenesis in vitro," Materials Science and Engineering: C 6, vol. 4, (1998), pp. 301-306.
Poonam, V., et al., "Agar-gelatin hybrid sponge-induced three-dimensional in vitro 'liver-like' HepG2 spheroids for the evaluation of drug cytotoxicity," J. Tissue Eng. Regen. Med. 4, (2010), pp. 524-531.
Rnjak-Kovacina, J. et al., "Lyophilized Silk Sponges: A Versatile Biomaterial Platform for Soft Tissue Engineering," ACS Biomater. Sci. Eng. 1, (2015), pp. 260-270.
Rohanizadeh, R., et al., "Gelatin sponges (Gelfoam(R)) as a scaffold for osteoblasts," J. Mater. Sci. Mater. Med. 19, (2008), pp. 1173-1182.
Shapiro, L. & Cohen, S., "Novel alginate sponges for cell culture and transplantation," Biomaterials 18, (1997) pp. 583-590.
Teuschl, A., et al., "Silk fibroin based carrier system for delivery of fibrinogen and thrombin as coagulant supplements," J. Biomed. Mater. Res.—Part A 105, (2017), pp. 687-696.
Whitehead, T., et al., "Artificial Tissue Bioreactor (ATB) for Biological and Imaging Applications," Engineering in Medicine and Biology Society (EMBC), 2012 Annual International Conference of the IEEE, IEEE, 2012, pp. 2420-2423.
Whitehead, T., et al., "A PET-Compatible Tissue Bioreactor for Research, Discovery, and Validation of Imaging Biomarkers and Radiopharmaceuticals: System Design and Proof-of-Concept Studies." Journal of Nuclear Medicine 54, vol. 10, (2013), pp. 1812-1819.
Widdowson, J., et al., "In vivo comparison of jellyfish and bovine collagen sponges as prototype medical devices," J. Biomed. Mater. Res.—Part B Appl. Biomater., (2017) 10 pages.
Communication received in European Application No. 19712214.6, dated Aug. 23, 2023.
Yeatts, A., et al., "Tubular Perfusion System for the Long-Term Dynamic Culture of Human Mesenchymal Stem Cells," vol. 17, No. 3, 2011, pp. 337-348.

DEVICE AND METHOD FOR MICRO-PET OR MICRO-SPECT OF A CELL CULTURE

BACKGROUND

The present invention relates to devices and methods for micro-positron emission tomography (micro-PET) or micro-single photon emission computed tomography (micro-SPECT) of a cell culture.

Current strategies for preclinical screening of potential diagnostic compounds for positron emission tomography (PET) or single emission computed tomography (SPECT) are mainly based on prior biological knowledge, ex vivo autoradiography, and in vivo PET or SPECT of small animals.

However, prediction of in vivo absorption, distribution, metabolism and excretion of compounds based on prior biological knowledge correlated to ex vivo autoradiography is still very limited. Promising lead compounds often have to be discontinued due to lack of selectivity to the target, fast metabolism and clearance, or unspecific interactions, based on the results of costly in vivo experiments. Therefore, there is a need for improved prediction of in vivo behaviour of such diagnostic compounds as well as therapeutic compounds, e.g. with better cell culture systems specifically adapted to PET/SPECT.

Keshari et al. relates to the metabolic response of prostate cancer to nicotinamide phosphoribosyltransferase inhibition in a hyperpolarised magnetic resonance/PET-compatible bioreactor. Disclosed is a perfusion bioreactor compatible with hyperpolarised magnetic resonance and PET to develop translatable biomarkers of response to nicotinamide phosphoribosyltransferase inhibition in reduced volume cell cultures. A single cell culture of prostate cancer cells was embedded into an alginate hydrogel and cultured in the bioreactor (p. 1603, left col, § 2). A small animal micro-PET/computer tomography (CT) scanner (Inveon, Siemens Medical Solutions) was used for PET imaging. Medium containing 5 µCi/ml of 2-deoxy-2-[$^{18}$F] fluoroglucose ([$^{18}$F] FDG) was perfused through the bioreactor system for 40 minutes and washed out for 40 minutes. For the purposes of higher throughput, four bioreactors were run concurrently in the PET detector, one containing empty alginate encapsulates as a control (p. 1604, left col, § 2). However, this approach is complicated, high in instrumentation load and therefore cost-intensive.

Whitehead et al., 2012, relates to an artificial tissue bioreactor for biological and imaging applications. The disclosed bioreactor is integrated with a micro-PET scanner. The cell chamber of the disclosed bioreactor is a glass vessel containing borosilicate glass beads with a diameter between 1.4 and 1.7 mm (p. 2420, right col, § 2). A single culture of the HepG2 liver cell line was drawn into a syringe and injected into the cell chamber of the bioreactor (p. 2421, left col, § 5). The cells were allowed to settle into the bead matrix for about 16 hours and allowed to expand for five days before being subjected to glucose tolerance tests and then to micro-PET scanning with [$^{11}$C] palmitate as a radiotracer (p. 2421, right col, § 1-5). Whitehead et al., 2013, discloses the same glass bead bioreactor for research, discovery, and validation of imaging biomarkers and radiopharmaceuticals. Throughput of this glass bead bioreactor is relatively low, however.

It is thus an object of the present invention to provide improved methods and devices for cell culture PET, especially to attain a higher measurement throughput.

SUMMARY

The present invention provides a method for concurrent micro-PET or micro-SPECT of at least two cell cultures in a biocompatible column. The column comprises an inlet, an axially oriented perfusion chamber and an outlet, both the inlet and the outlet being fluidly connected to the perfusion chamber. The perfusion chamber comprises a porous solid phase, in aqueous liquid phase, a first cell culture and a second cell culture. At least a portion of the first cell culture (e.g. at least 1%, preferably at least 5%, more preferably at least 10%, even more preferably at least 20%, yet even more preferably at least 30%, especially at least 40% or even at least 50% of the surface of the cell culture, e.g. the MTS) and at least a portion of the second cell culture (e.g. at least 1%, preferably at least 5%, more preferably at least 10%, even more preferably at least 20%, yet even more preferably at least 30%, especially at least 40% or even at least 50% of the surface of the cell culture, e.g. the MTS) are in contact with the solid phase; another portion of the first and second cell culture, respectively, is typically in contact with the liquid phase. The first cell culture is separated from the second cell culture by at least a portion of the solid phase. The method comprises the following steps:

(A) inserting the column into a micro-PET or micro-SPECT scanner;

(B) conducting an aqueous labelling liquid comprising a radioactive tracer via the inlet through the perfusion chamber towards the outlet, such that at least a portion of the cells of the first cell culture and at least a portion of the cells of the second cell culture are contacted with the radioactive tracer (preferably, a fraction, e.g. at least 0.5% or at least 5% or at least 10% by weight, of the radioactive tracer remains bound to the first and/or the second cell culture; such binding may be extracellularly and/or intracellularly);

(C) conducting an aqueous washing liquid via the inlet through the perfusion chamber towards the outlet, such that at least a portion of the radioactive tracer is removed from the perfusion chamber through the outlet; and (D) scanning the column with the micro-PET or micro-SPECT scanner.

Different orders of the steps, such as B-C-A-D or B-A-C-D, are also encompassed by this method. The order A-B-C-D is the most preferred, though.

The present invention also provides a biocompatible column for concurrent micro-PET or micro-SPECT of at least two cell cultures. The column comprises an inlet, an axially oriented perfusion chamber and an outlet, both the inlet and the outlet being fluidly connected to the perfusion chamber. The perfusion chamber comprises a porous solid phase which comprises at least one (preferably at least two, more preferably at least three, even more preferably at least four, yet even more preferably at least five, especially at least six) sponge comprising (in particular made of) at least one biopolymer. The perfusion chamber further comprises an aqueous liquid phase, a first cell culture and a second cell culture. At least a portion of the first cell culture (e.g. at least 1%, preferably at least 5%, more preferably at least 10%, even more preferably at least 20%, yet even more preferably at least 30%, especially at least 40% or even at least 50% of the surface of the cell culture, e.g. the MTS) and at least a portion of the second cell culture (e.g. at least 1%, preferably at least 5%, more preferably at least 10%, even more preferably at least 20%, yet even more preferably at least 30%, especially at least 40% or even at least 50% of the surface of the cell culture, e.g. the MTS) are in contact with the solid phase; another portion of the first and second cell culture, respectively, is typically in contact with the liquid phase. The first cell culture is separated from the second cell culture by at least a portion of the solid phase.

In another aspect of the present invention, a system for concurrent micro-PET or micro-SPECT of at least two cell cultures is provided. The system comprises the column of the present invention, wherein the column is fluidly connected to a pump via its inlet and/or its outlet. Preferably, the system further has a temperature control for the column and/or a sample injector fluidly connected to the inlet of the column.

In yet another aspect of the present invention, a micro-PET or micro-SPECT scanner with the column of the present invention inserted is provided.

In even yet another aspect of the present invention, a kit for concurrent micro-PET or micro-SPECT of at least two cell cultures is provided. The kit comprises at least one biocompatible column for concurrent micro-PET or micro-SPECT of at least two cell cultures, the column comprising an inlet, an axially oriented perfusion chamber and an outlet, both the inlet and the outlet being fluidly connected to the perfusion chamber. The kit further comprises at least two (preferably at least three, even more preferably at least five, yet even more preferably at least ten, especially at least 20) sponges comprising (in particular made of) at least one biopolymer, which biopolymer is preferably selected from silk, silk fibroin, collagen, gelatin, agarose, alginate, polylactic acid, agar, methylcellulose and mixtures thereof. These sponges are pre-cut to fit into the perfusion chamber.

The present invention enables PET (and also SPECT) of cell cultures (even three-dimensional cell cultures such as spheroids and organoids) with a higher throughput. The present invention is highly suitable for accelerated radioactive tracer (radiotracer) development. It is particularly useful for measuring accumulation, tissue penetration, target specificity as well as for metabolism studies of radiotracers with cells or multicellular tumour spheroids (MTS) in a biomatrix. Furthermore, the present invention allows conditioning of flow rates to stimulate blood flow within a complex tissue sample. The present invention also serves to reduce the number of animals needed in preclinical drug development, thereby making such development more efficient and reducing ethical concerns.

Entirely unrelated to PET or SPECT imaging, Mizuno et al. describe a hydrostatic pressure system for the application of hydrostatic fluid pressure to chondrocytes in 3D collagen sponges. The system comprises a column through which hydrostatic fluid pressure can be applied. Chondrocytes are cultured in collagen sponges, which are suspended in said column. The disclosed system would not be suitable for PET or SPECT imaging, i.a. because imaging artifacts would be expected resulting from impaired washout of the solution accumulating around the attachment positions of the sponges.

Also completely unrelated to PET or SPECT imaging, US 2017/198246 A1 discloses a small perfusion bioreactor comprising a container for holding cell culture medium connected to a capture column containing a product binding medium. The capture column allows capture of the expressed product as the culture medium flows out of the container and through the column. The cell culture merely passes through the column as the culture medium is drained out and is thus not retained in the column.

Micro-PET and micro-SPECT devices are miniaturised PET and SPECT devices, respectively, developed for imaging research applications on rodents and other small-animal models (an overview over these technologies is given e.g. in Chatziioannou). Typically, the spatial resolution of micro-PET and micro-SPECT is higher than that of generic PET and SPECT devices (for imaging of human patients). Micro-PET and micro-SPECT imaging functionality can also be combined in a single device, optionally with additional imaging functionalities such as CT (i.e. micro-PET/SPECT/CT), see e.g. Koba et al. At least micro-PET can also be combined with magnetic resonance imaging (MRI) in a single device (i.e. micro-PET/MRI).

Due to their high resolution, these devices can also be used to image cell cultures (see e.g. Keshari et al., Whitehead et al., 2012 and Whitehead et al., 2013, already described above).

Preferably, in the context of the present invention, a "micro-PET scanner" is a PET scanner with a transaxial field of view (FOV) diameter below 50 cm, preferably below 40 cm, more preferably below 30 cm, even more preferably below 25 cm, yet even more preferably below 20 cm, especially below 15 cm or even below 10 cm (but usually more than 1 cm or 2 cm) and/or reconstructed resolution at the centre of the FOV below 4 mm, preferably below 3 mm, more preferably below 2 mm, especially below 1.5 mm (typically, this resolution is around 1 mm). The term "micro-PET" alone thus relates to PET measurement in a micro-PET scanner. In the context of the present invention, the micro-PET scanner may also have additional imaging functionalities such as MRI, SPECT and/or CT, i.e. it may be e.g. a micro-PET/CT or micro-PET/SPECT/CT or micro-PET/MRI scanner.

Preferably, in the context of the present invention, a "micro-SPECT scanner" is a SPECT scanner with a spatial resolution below 4 mm, preferably below 3 mm, more preferably below 2 mm, especially below 1.5 mm or even below 1.0 mm (typically, this resolution is around 0.75 mm). The term "micro-SPECT" alone thus relates to SPECT measurement in a micro-SPECT scanner. In the context of the present invention, the micro-SPECT scanner may also have additional imaging functionalities such as PET and/or CT, i.e. it may be e.g. a micro-SPECT/CT or micro-PET/SPECT/CT scanner.

In the context of the present invention, the (first and/or second) cell culture may for instance be a primary cell culture, e.g. derived from a biopsy from a mammalian, preferably human, patient such as a cancer patient. The (first and/or second) cell culture may also be e.g. a cell culture of a cell line, such as a mammalian or human cell line. The (first and/or second) cell culture may for instance also be a co-culture of different cell types. The first and second cell culture may be of the same cell type (e.g. to have biological replicates in the same perfusion chamber) or of different cell types (e.g. to study the effect of the radioactive tracer on different cell types within the same perfusion chamber).

Preferably, the first cell culture and/or the second cell culture is a three-dimensional cell culture, especially a spheroid or organoid. In particular, the first cell culture and/or the second cell culture is an MTS (see e.g. Hirschhaeuser et al.). The present invention is particularly suitable for these types of cell cultures.

In a preferred embodiment of the present invention, the column comprises at least three, preferably at least four, more preferably at least five of said cell cultures. This further increases measurement throughput of the present invention. For instance, the column may comprise five sponges, each in contact with another cell culture (e.g. comprising the respective cell culture in its recess) and another sponge not in contact with a cell culture.

Within the context of the present invention, the radioactive tracer is a positron-emitting compound (such as a compound containing at least one $^{18}F$, $^{11}C$, $^{13}N$, $^{15}O$, $^{82}Rb$ or $^{68}Ga$) or a gamma-emitting compound (such as a compound containing at least one $^{99m}Tc$, $^{177}Lu$, $^{123}I$, $^{131}I$ or $^{111}In$). Commonly used radioactive tracers for PET are for instance 2-deoxy-2-[$^{18}F$] fluoroglucose, [$^{18}F$] fluoroalkylcholine, [$^{18}F$] fluorouracil, [$^{68}Ga$] edotreotide and [$^{11}C$] acetate. Commonly used radioactive tracers for SPECT are for instance [$^{99m}Tc$] sestamibi or [$^{123}I$]-meta-iodobenzylguanidine. However, the present invention is not limited to commonly used radioactive tracers.

Preferably, the aqueous labelling liquid is a buffered solution of the radioactive tracer, in particular with a physiological pH, e.g. the radioactive tracer in phosphate-buffered saline (PBS) or in growth medium. Preferably, the aqueous washing liquid is a buffered solution, in particular with a physiological pH, e.g. PBS or growth medium. Most typically, the washing solution does not contain any radioactive tracer.

In a particularly preferred embodiment of the present invention, the porous solid phase present in the perfusion chamber of the column comprises at least one (preferably at least two, more preferably at least three, even more preferably at least four, yet even more preferably at least five, especially at least six) sponge comprising (in particular made of) at least one biopolymer. This biopolymer is preferably selected from silk, silk fibroin, collagen, gelatin, agarose, alginate, polylactic acid, agar, methylcellulose and mixtures thereof. Such sponges are e.g. disclosed in Rnjak-Kovacina et al., Widdowson et al., Rohanizadeh et al., Shapiro et al., Carfi-Pavia et al. and Poonam et al. In the course of the present invention, silk fibroin sponges turned out to be especially suitable for supporting cell cultures, in particular three-dimensional cell cultures such as MTS, within the inventive column during PET or SPECT analysis, while showing only low interactions with radioactive tracers. Silk fibroin sponges are for instance disclosed in Teuschl et al. It is especially preferred that the sponge is pre-cut to fit into the perfusion chamber. For instance, if the perfusion chamber has a circular profile, the sponges can be pre-cut by punching device with a circular blade.

Within the context of the present invention, the sponge(s) preferably have a maximum diameter between 0.5 mm and 50 mm, preferably between 1 mm and 40 mm, more preferably between 1.5 mm and 25 mm, especially between 2 mm and 10 mm.

In a further preferred embodiment of the present invention, the porous solid phase (e.g. at least one sponge) has an average pore diameter between 50 µm and 1000 µm, preferably between 75 µm and 750 µm, more preferably between 100 µm and 600 µm, even more preferably between 125 µm and 500 µm, yet even more preferably between 150 µm and 450 µm, especially between 200 µm and 400 µm. The mentioned average pore diameter range turned out to be suitable for supporting the cells while still allowing for an appropriate flow rate through the perfusion chamber.

As the spatial resolution of micro-PET and micro-SPECT is limited, it is advantageous when the cell cultures in the perfusion chamber have a sufficient distance from each other such that the signal of the radioactive tracer bound to the first cell culture is not disturbed significantly by the signal of the radioactive tracer bound to the second cell culture. A minimal distance between 600 µm and 5000 µm was found to be particularly effective. Therefore, in a preferred embodiment, the minimal distance between the first cell culture and the second cell culture is at least 600 µm, preferably at least 700 µm, more preferably at least 800 µm, even more preferably at least 900 µm, yet even more preferably at least 1000 µm, especially at least 2000 µm or even at least 5000 µm.

According to an especially preferred embodiment of the present invention, the porous solid phase comprises at least a first and a second of said sponges. In this embodiment, at least a portion of the first culture (e.g. at least 1%, preferably at least 5%, more preferably at least 10%, even more preferably at least 20%, yet even more preferably at least 30%, especially at least 40% or even at least 50% of the surface of the cell culture, e.g. the MTS) is in contact with the first sponge and at least a portion of the second culture (e.g. at least 1%, preferably at least 5%, more preferably at least 10%, even more preferably at least 20%, yet even more preferably at least 30%, especially at least 40% or even at least 50% of the surface of the cell culture, e.g. the MTS) is in contact with the second sponge. Preferably, at least a portion of the first culture (e.g. at least 1%, preferably at least 5%, more preferably at least 10%, even more preferably at least 20%, yet even more preferably at least 30%, especially at least 40% or even at least 50% of the surface of the cell culture, e.g. an MTS) is attached to the first sponge and at least a portion of the second culture (e.g. at least 1%, preferably at least 5%, more preferably at least 10%, even more preferably at least 20%, yet even more preferably at least 30%, especially at least 40% or even at least 50% of the surface of the cell culture, e.g. an MTS) is attached to the second sponge. Herein, the expression of the cell culture being "attached" to the sponge shall mean that at least a portion of the cells (e.g. at least 1%, preferably at least 5%, more preferably at least 10%, even more preferably at least 20%, yet even more preferably at least 30%, especially at least 40% or even at least 50% of the surface of the cell culture, e.g. an MTS) of the cell culture have formed an attachment to the sponge by their cell adhesion molecules (CAMs) such as selectins, integrins or cadherins. Such cell adhesion may for instance be promoted by incubating the cell culture when it is in contact with the sponge in growth medium at 37° C. for 2 to 3 hours.

In another preferment, the first sponge has a recess comprising at least a portion of the first culture (e.g. at least 5%, preferably at least 10%, more preferably at least 25%, even more preferably at least 50%, yet even more preferably at least 75%, especially at least 90% or even at least 95% of the volume of the cell culture, e.g. an MTS) and the second sponge has a recess comprising at least a portion of the second cell culture (e.g. at least 5%, preferably at least 10%, more preferably at least 25%, even more preferably at least 50%, yet even more preferably at least 75%, especially at least 90% or even at least 95% of the volume of the cell culture, e.g. an MTS). This recess serves to enhance the favourable interactions between the cell culture and the biopolymer of the sponge by increasing the interaction surface between them as well as stabilising the cell culture in its position. Typically, the maximum diameter of the recess is larger than the average pore diameter of the porous solid phase (and/or of the sponge which has the recess), preferably at least 2× as large, more preferably at least 3× as large, yet even more preferably at least 4× as large, especially at least 5× as large. For instance, the recess may have a maximum diameter of more than 1 mm, or even more than 2 mm, especially of more than 3 mm.

In order to identify individual cell cultures in the PET or SPECT scans, the column comprises, in a preferred embodiment, an additional radioactive label or a radiopaque label to indicate the position of at least one of the cell cultures in the column. If the label is radioactive, e.g. a positron-emitting compound (such as a compound containing at least one $^{18}$F, $^{11}$C, $^{13}$N, $^{15}$O, $^{82}$Rb or $^{68}$Ga) or a gamma-emitting compound (such as a compound containing at least one $^{99m}$Tc, $^{123}$I, $^{131}$I or $^{111}$In), the label is preferably present in solution, e.g. in aqueous solution. Advantageously, the column comprises an additional chamber containing the radioactive label, preferably in the form of a solution. If the label is radiopaque (in particular with respect to x-rays, e.g. for use in micro-PET/CT or micro-SPECT/CT, such as for superimposition of the PET image and the CT image), e.g. a metal oxide such as zirconium dioxide, barium sulphate, ferrite, magnetite, potassium salts, or heavy metal particulates, then the label is preferably present as a solid, e.g. in the form of small plates or discs. Advantageously, the column comprises an additional chamber containing the radioactive label, preferably in the form of small plates or discs.

By way of example, the column may comprise several empty (small) chambers along the axis of the perfusion chamber. The perfusion chamber is filled with the sponges, each loaded with a cell culture. For each cell culture, only the chamber closest to the cell culture is filled with a solution with the radioactive label or with a radiopaque plate or disc. In the PET or SPECT scan (or in the superimposed CT scan), these chambers will be detected and serve as an additional control, indicating the position of each cell culture. Of course, the characteristics of the chamber may depend on whether it is to be filled with a solution or with plates or discs.

In another preferred embodiment, the perfusion chamber further comprises at least one solid marker indicating the position of at least one of the cell cultures in the column. This solid marker has a higher density than the porous solid phase (e.g. the sponges), preferably at least 1.25× as high, more preferably at least 1.5× as high, especially at least 2× as high. This allows for easier identification of the cell cultures in imaging methods. Of course, the solid marker does not completely inhibit flow in the perfusion chamber. Therefore, the solid marker is preferably porous. For instance, the solid marker may be a filter (see e.g. FIG. 7). The solid marker may be located between two of the sponges (see also FIG. 7). When calculating their respective density, the content of the pores of the porous solid phase and the content of the pores of the porous solid marker (if any) shall be taken into account, respectively, i.e. considering the total mass of the material vs. its volume when its pores are filled with water.

According to a further preferred embodiment, at least a portion of the column is transparent, preferably such that at least a portion of the contents of the perfusion chamber is visible from the outside. This is useful for checking the status of the perfusion chamber, e.g. before inserting the column into the PET or SPECT scanner.

According to a further preferred embodiment, the first cell culture has a higher binding affinity to the radioactive tracer than the second cell culture.

In the context of the inventive method, it is preferred that conducting of step (B) and/or step (C) comprises turbulent liquid flow (as opposed to laminar flow) through the perfusion chamber, preferably with a flow rate of 0.01 ml/min to 10 ml/min, preferably 0.025 ml/min to 7.5 ml/min, more preferably 0.05 ml/min to 5 ml/min, especially 0.1 ml/min to 2 ml/min. Turbulent flow turned out to lead to a situation for the cell cultures which is closer to the physiological situation (i.e. liquid flow through tissue is typically turbulent). This is a crucial advantage of the present invention over microfluidic systems which almost always have laminar liquid flow.

Turning to the kit aspect of the present invention specifically, the kit may further comprise usage instructions, e.g. instructions to use the column of the kit in a PET or SPECT scanner, in particular instructions to use the kit according to the inventive method. Preferably, the inventive kit further comprises at least two filters which are pre-cut to fit into the perfusion chamber of the column of the kit. According to further preference, the kit further comprises at least one sterile filter, i.e. a filter with an average pore size below 1 µm, preferably below 0.5 µm, especially below 0.25 µm. This sterile filter e.g. may be attached to the inlet and/or the outlet of the column. The inventive kit may also comprise tubing.

The inventive kit may also comprise at least one of the radiopaque label discussed above, for instance in the form of small plates or discs. Especially in this case, the column may have additional chambers for optional filling with the radiopaque labels.

Within the context of the present invention, the column preferably has a diameter between 0.5 mm and 20 mm, preferably between 1 mm and 10 mm, especially between 2 mm and 8 mm.

Furthermore, within the context of the present invention, it is highly preferred that the porous solid phase does not comprise a hydrogel. Alternatively, or in addition thereto, the porous solid phase preferably has irregular pores.

Herein, the expression "biocompatible column" shall preferably mean that the surfaces of the column (e.g. in the perfusion chamber) which come into contact with the cell cultures during use do not (significantly) inhibit cell growth, i.e. they are not (significantly) cytotoxic.

The present invention further relates to the following embodiments:

Embodiment 1. A method for concurrent micro-positron emission tomography (micro-PET) or micro-single photon emission computed tomography (micro-SPECT) of at least two cell cultures in a biocompatible column,
the column comprising an inlet, an axially oriented perfusion chamber and an outlet, wherein the inlet is fluidly connected to the perfusion chamber and the outlet is fluidly connected to the perfusion chamber, wherein the perfusion chamber comprises a porous solid phase, an aqueous liquid phase, a first cell culture and a second cell culture, wherein at least a portion of the first cell culture and at least a portion of the second cell culture are in contact with the solid phase and wherein the first cell culture is separated from the second cell culture by at least a portion of the solid phase;
the method comprising the steps of
(A) inserting the column into a micro-PET or micro-SPECT scanner;
(B) conducting an aqueous labelling liquid comprising a radioactive tracer via the inlet through the perfusion chamber (3) towards the outlet, such that at least a portion of the cells of the first cell culture and at least a portion of the cells of the second cell culture are contacted with the radioactive tracer;
(C) conducting an aqueous washing liquid via the inlet through the perfusion chamber towards the outlet, such that at least a portion of the radioactive tracer is removed from the perfusion chamber through the outlet; and
(D) scanning the column with the micro-PET or micro-SPECT scanner.

Embodiment 2. The method of embodiment 1, wherein the first cell culture and/or the second cell culture is a spheroid or an organoid.

Embodiment 3. The method of embodiment 2, wherein the first cell culture and/or the second cell culture is a multicellular tumour spheroid (MTS).

Embodiment 4. The method of any one of embodiments 1 to 3, wherein the conducting of step (B) and/or step (C) comprises turbulent liquid flow through the perfusion chamber, preferably with a flow rate of 0.01 ml/min to 10 ml/min, preferably 0.025 ml/min to 7.5 ml/min, more preferably 0.05 ml/min to 5 ml/min, especially 0.1 ml/min to 2 ml/min.

Embodiment 5. The method of any one of embodiments 1 to 4, wherein the porous solid phase comprises at least one sponge comprising at least one biopolymer, preferably wherein the biopolymer is selected from silk, silk fibroin, collagen, gelatin, agarose, alginate, polylactic acid, agar, methyl-cellulose and mixtures thereof and/or wherein the is pre-cut to fit into the perfusion chamber.

Embodiment 6. The method of any one embodiments 1 to 5, wherein the porous solid phase has an average pore diameter between 50 μm and 1000 μm, preferably between 75 μm and 750 μm, more preferably between 100 μm and 600 μm, even more preferably between 125 μm and 500 μm, yet even more preferably between 150 μm and 450 μm, especially between 200 μm and 400 μm.

Embodiment 7. The method of any one of embodiments 1 to 6, wherein the minimal distance between the first cell culture and the second cell culture is at least 600 μm, preferably at least 700 μm, more preferably at least 800 μm, even more preferably at least 900 μm, yet even more preferably at least 1000 μm, especially at least 2000 μm or even at least 5000 μm.

Embodiment 8. The method of any one of embodiments 5 to 7, wherein the porous solid phase comprises at least a first and a second of said sponges, wherein at least a portion of the first culture is in contact with the first sponge and at least a portion of the second culture is in contact with the second sponge.

Embodiment 9. The method of embodiment 8, wherein at least a portion of the first culture is attached to the first sponge and at least a portion of the second culture is attached to the second sponge.

Embodiment 10. The method of embodiment 8 or 9, wherein the first sponge has a recess comprising at least a portion of the first cell culture and the second sponge has a recess comprising at least a portion of the second cell culture.

Embodiment 11. The method of any one of embodiments 1 to 10, wherein the column comprises an additional radioactive or radiopaque label indicating the position of at least one of the cell cultures in the column.

Embodiment 12. The method of embodiment 11, wherein the column comprises an additional chamber containing the radioactive or radiopaque label.

Embodiment 13. The method of any one of embodiments 1 to 12, wherein the perfusion chamber further comprises at least one solid marker indicating the position of at least one of the cell cultures in the column, wherein the solid marker has a higher density than the porous solid phase, preferably at least 1.25× as high, more preferably at least 1.5× as high, especially at least 2× as high.

Embodiment 14. The method of any one of embodiments 1 to 13, wherein at least a portion of the column is transparent.

Embodiment 15. The method of any one of embodiments 1 to 14, wherein the first cell culture has a higher binding affinity to the radioactive tracer than the second cell culture.

Embodiment 16. A biocompatible column for concurrent micro-PET or micro-SPECT of at least two cell cultures, the column comprising an inlet, an axially oriented perfusion chamber and an outlet, wherein the inlet is fluidly connected to the perfusion chamber and the outlet is fluidly connected to the perfusion chamber, wherein the perfusion chamber comprises a porous solid phase comprising at least one sponge comprising at least one biopolymer, an aqueous liquid phase, a first cell culture and a second cell culture, wherein at least a portion of the first cell culture and at least a portion of the second cell culture are in contact with the solid phase and wherein the first cell culture is separated from the second cell culture by at least a portion of the solid phase.

Embodiment 17. The column of embodiment 16, wherein the first cell culture and/or the second cell culture is a spheroid or an organoid.

Embodiment 18. The column of embodiment 17, wherein the first cell culture and/or the second cell culture is an MTS.

Embodiment 19. The column of any one of embodiments 16 to 18, wherein the biopolymer is selected from silk, silk fibroin, collagen, gelatin, agarose, alginate, polylactic acid, agar, methyl-cellulose and mixtures thereof.

Embodiment 20. The column of embodiment 19, wherein the biopolymer is silk fibroin.

Embodiment 21. The column of any one of embodiments 16 to 20, wherein the sponge is pre-cut to fit into the perfusion chamber.

Embodiment 22. The column of any one of embodiments 16 to 21, wherein the porous solid phase has an average pore diameter between 50 μm and 1000 μm, preferably between 75 μm and 750 μm, more preferably between 100 μm and 600 μm, even more preferably between 125 μm and 500 μm, yet even more preferably between 150 μm and 450 μm, especially between 200 μm and 400 μm.

Embodiment 23. The column of any one of embodiments 16 to 22, wherein the minimal distance between the first cell culture and the second cell culture is at least 600 μm, preferably at least 700 μm, more preferably at least 800 μm, even more preferably at least 900 μm, yet even more preferably at least 1000 μm, especially at least 2000 μm or even at least 5000 μm.

Embodiment 24. The column of any one of embodiments 16 to 23, wherein the porous solid phase comprises at least a first and a second of said sponges, wherein at least a portion of the first culture is in contact with the first sponge and at least a portion of the second culture in contact with the second sponge.

Embodiment 25. The column of embodiment 24, wherein at least a portion of the first culture is attached to the first sponge and at least a portion of the second culture is attached to the second sponge.

Embodiment 26. The column of embodiment 24 or 25, wherein the first sponge has a recess comprising at least a portion of the first cell culture and the second sponge has a recess comprising at least a portion of the second cell culture.

Embodiment 27. The column of any one of embodiments 16 to 26, wherein the column comprises an additional radioactive or radiopaque label indicating the position of at least one of the cell cultures in the column.

Embodiment 28. The column of embodiment 27, wherein the column comprises an additional chamber containing the radioactive or radiopaque label.

Embodiment 29. The column of any one of embodiments 16 to 28, wherein the perfusion chamber further comprises at least one solid marker indicating the position of at least one of the cell cultures in the column, wherein the solid marker has a higher density than the porous solid phase, preferably at least 1.25× as high, more preferably at least 1.5× as high, especially at least 2× as high.

Embodiment 30. The column of any one of embodiments 16 to 29, wherein at least a portion of the column is transparent.

Embodiment 31. The column of any one of embodiments 16 to 30, wherein the first cell culture has a higher binding affinity to the radioactive tracer than the second cell culture.

Embodiment 32. A system for concurrent micro-PET or micro-SPECT of at least two cell cultures, comprising the column of any one of embodiments 16 to 30 fluidly connected to a pump via the inlet and/or the outlet, preferably wherein the system further has a temperature control for the column and/or a sample injector fluidly connected to the inlet of the column.

Embodiment 33. A micro-PET or micro-SPECT scanner with the column of any one of embodiments 16 to 30 inserted.

Embodiment 34. A kit for concurrent micro-PET or micro-SPECT of at least two cell cultures, comprising:

at least one biocompatible column for concurrent micro-PET or micro-SPECT of at least two cell cultures, the column comprising an inlet, an axially oriented perfusion chamber and an outlet, wherein the inlet is fluidly connected to the perfusion chamber and the outlet is fluidly connected to the perfusion chamber; and at least two sponges comprising at least one biopolymer, preferably selected from silk, silk fibroin, collagen, gelatin, agarose, alginate, polylactic acid, agar, methyl-cellulose and mixtures thereof, wherein the sponges are pre-cut to fit into the perfusion chamber.

Embodiment 35. The kit of embodiment 34, further comprising at least two filters pre-cut to fit into the perfusion chamber, preferably wherein the filters have a higher density than the at least two sponges, more preferably at least 1.25× as high, even more preferably at least 1.5× as high, especially at least 2× as high.

Embodiment 36. The kit of embodiment 34 or 35, further comprising at least one sterile filter.

BRIEF DESCRIPTION OF THE DRAWINGS

The present invention is further illustrated by the following figures and examples, without being restricted thereto.

DETAILED DESCRIPTION

Example 1—Biocompatible Column

Figure 1:
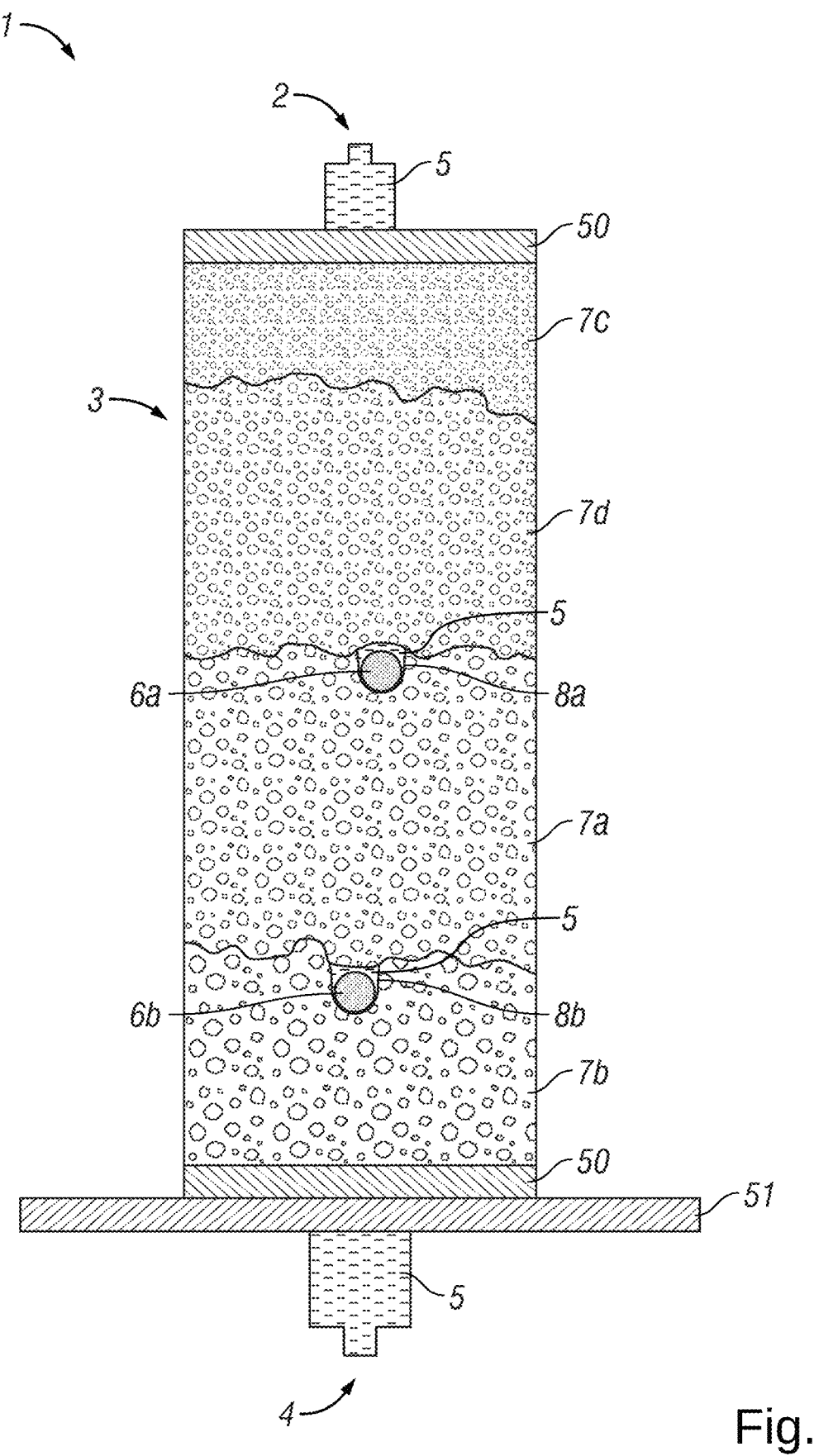
FIG. 1: Embodiment of the biocompatible column of the present invention.

FIG. 1 shows the biocompatible column 1 for concurrent micro-PET or micro-SPECT of the first cell culture 6a and the second cell culture 6b, which are both MTS. The column comprises the inlet 2, the axially oriented perfusion chamber 3 and the outlet 4. Both the inlet 2 and the outlet 4 are fluidly connected to the perfusion chamber 3. The perfusion chamber 3 comprises porous solid phase formed by four sponges, 7c, 7d, 7a, 7b, made of a biopolymer and which were pre-cut to fit into perfusion chamber 3. The liquid phase 5 consisting of growth medium extends from the inlet 2 through sponges 7c, 7d, 7a, 7b to the outlet 4. Sponges 7a and 7b have recesses 8a and 8b, respectively. The first cell culture 6a is located within recess 8a being in contact with sponge 7a, and the second cell culture 6b is located within recess 8b being in contact with sponge 7b. Sponges 7c and 7d neither have a recess nor a cell culture. The first cell culture 6a and the second cell culture 6b our separated from each other by sponge 7a. The column 1 further has one filter 50 adjacent to the inlet 2 and another filter 50 adjacent to sterile filter 51, which is adjacent to the outlet 4.

Figure 2:
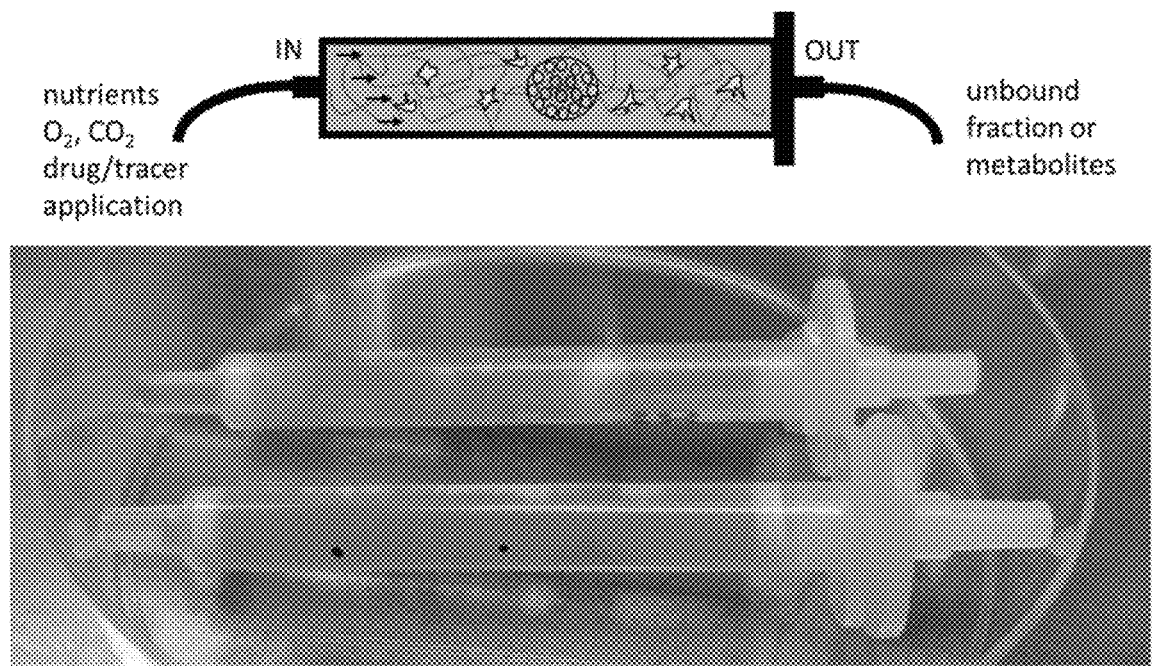
FIG. 2: Scheme and photograph of prototypes of the inventive biocompatible column. The column has a plastic housing as well as frits, the plastic housing forming a perfusion chamber with a solid porous phase consisting of several silk fibroin sponges as well as a liquid phase consisting of cell growth medium. The two dots on the lower column in the photograph indicate the presence of two cell cultures in the recesses of the sponges (MTS with about 1 mm diameter each).

Example 2—System for Concurrent Micro-PET or Micro-SPECT of at Least Two Cell Cultures The main objective of the system is to facilitate in vitro drug and especially PET or SPECT tracer development by providing a method applicable for assessment of drug distribution, accumulation, metabolism and excretion in a 3D bioscaffold with interstitial stop-flow conditions. The system consists of a mobile phase, which delivers nutrients, $O_2$ and $CO_2$ as well as the drug/tracer or modifiers over a constant flow through a biological stationary phase consisting of cells, MTS or organoids embedded in biopolymer sponges. A prototype of the column with the biological stationary phase is shown in FIG. 2.

Figure 3:
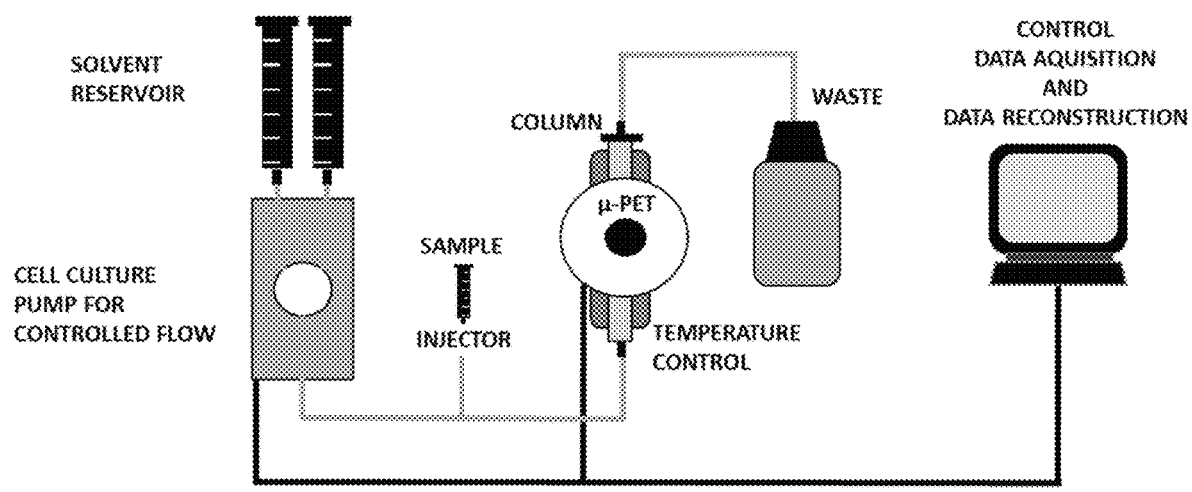
FIG. 3: Conceptual design of a fully automated system for concurrent micro-PET of at least two cell cultures, including a pump system for transportation of the liquid phase, injector valve for injection of the radioactive tracer, the biocompatible column with the cell cultures, micro-PET (µPET) as detection system, and a waste bottle. Several components are connected to a computer for process control, data acquisition and reconstruction.

The system furthermore comprises a controllable pump system, an apparatus to fixate the column and control the temperature, as well as a micro-PET scanner as detection unit (see FIG. 3).

Figure 4:
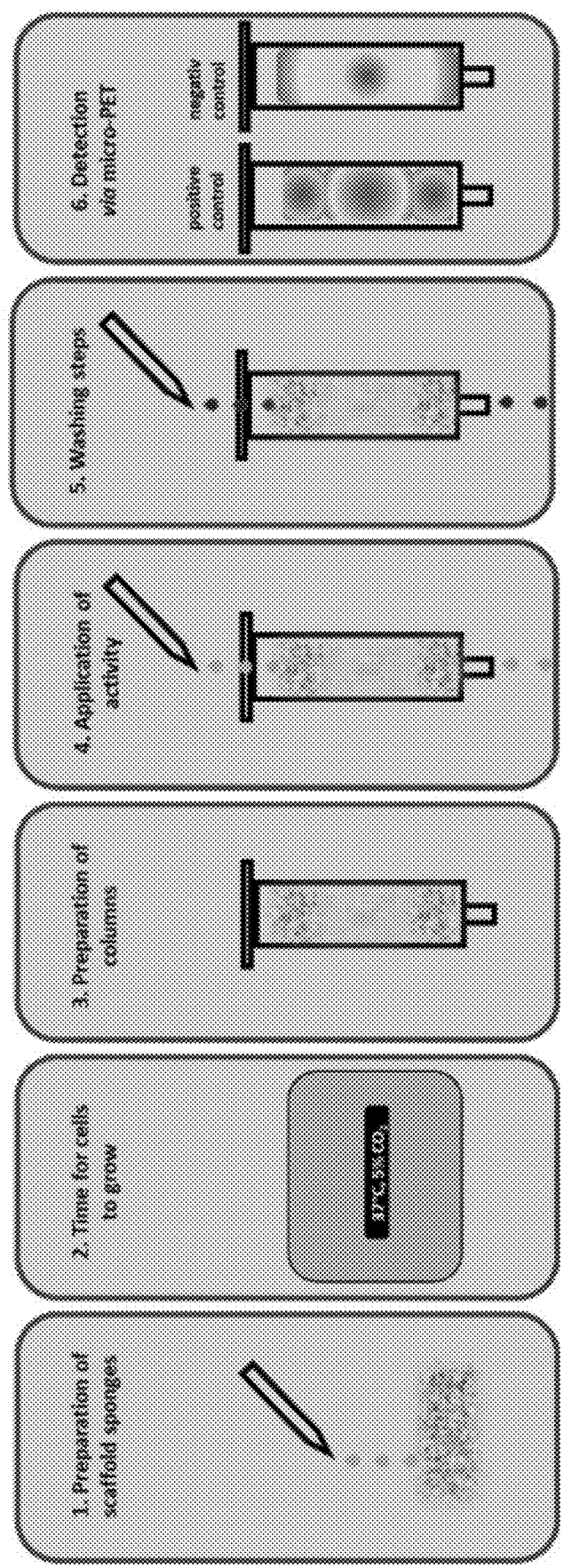
FIG. 4: Example for preparation of the biocompatible column. 1) Cell culture suspension is applied to the sponges; 2) cells are allowed to settle for at least 6 h; 3) sponge is inserted into the column and wetted with culture media; 4) the radioactive tracer is applied in a stop-flow mechanism; 5) removing residual radioactive tracer; 6) detection of radioactive tracer accumulation.

An example for preparation of the biocompatible column is shown in FIG. 4.

Example 3—Experimental Results

Figure 5:
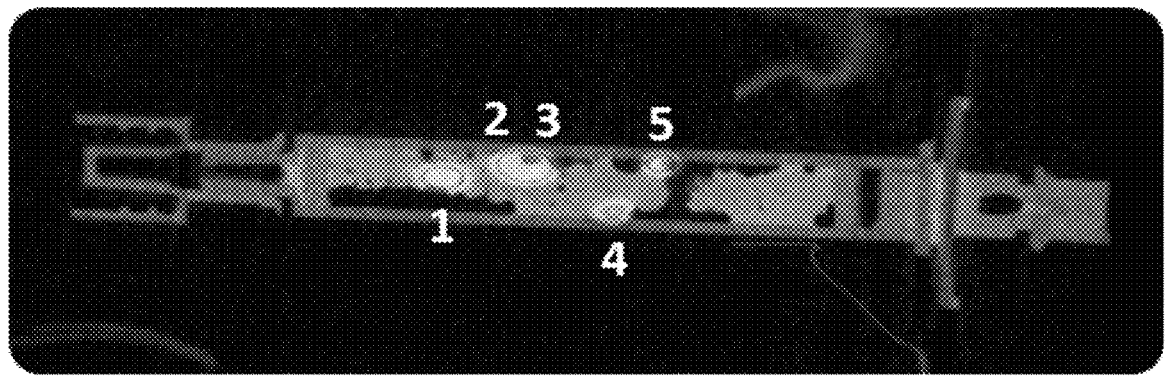
FIG. 5: PET scan of the inventive column loaded with five MTS. An aqueous solution [$^{18}$F] FDG was manually transferred through the porous solid phase with the five MTS (~700 µm in diameter each). After an incubation time of 60 min the unbound [$^{18}$F] FDG was washed out and the column was afterwards inserted into a micro-PET scanner and scanned. MTS 2 and 3, which were in close proximity to each other, could not be distinguished, whereas MTS 1, 4, and 5 could be well separated with exceptional signal-to-noise ratio.
Figure 6:
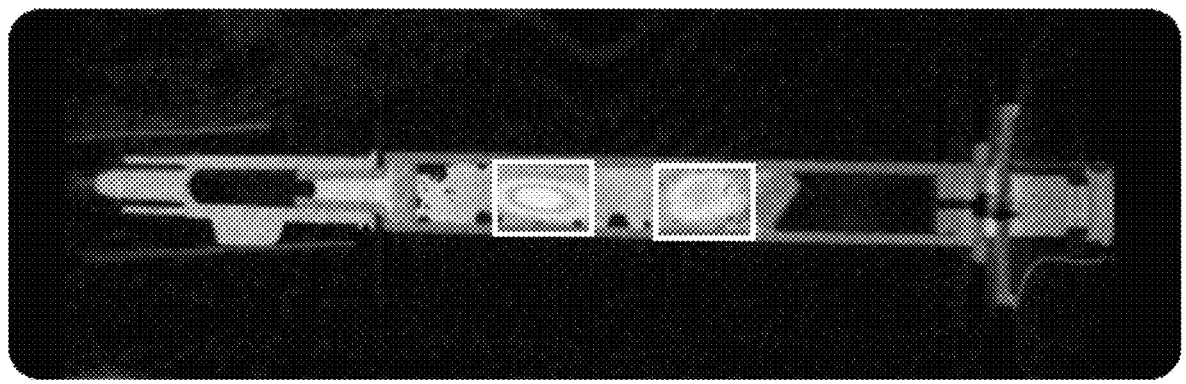
FIG. 6: PET scan of the inventive column loaded with two cell cultures (cells of HT29 human colorectal adenocarcinoma cell line seeded on two different silk sponges). An aqueous solution with [$^{18}$F] FDG was manually transferred through the porous solid phase with five MTS (~700 µm in diameter each). After an incubation time of 60 min the unbound [$^{18}$F] FDG was washed out and the column was subsequently inserted into a micro-PET scanner and scanned. The two HT29 cell cultures can be clearly distinguished from each other in the scan.
Figure 7:
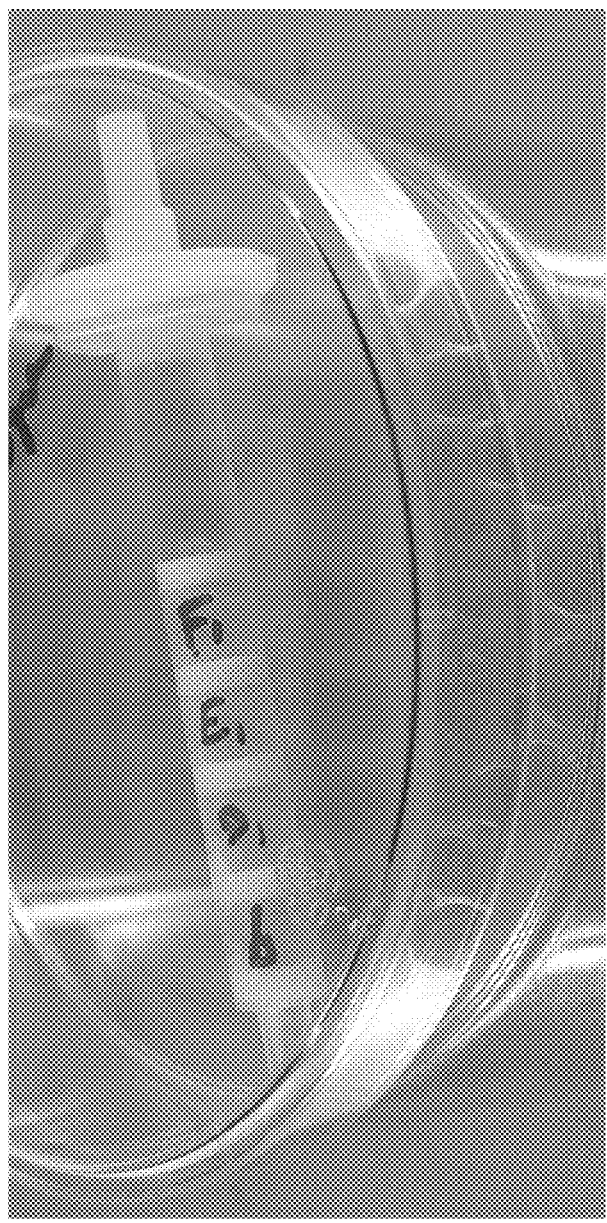
FIG. 7: Photograph of another prototype of the inventive column. The column has a plastic housing as well as frits, the plastic housing forming a perfusion chamber with a solid porous phase consisting of four silk fibroin sponges (indicated by the labels written onto the column) and filters (white material in the perfusion chamber) as well as a liquid phase consisting of cell growth medium. Each silk fibroin sponge contains in its recess an MTS with about 0.5 mm diameter. Each sponge has two filters adjacent to it. The filters have a higher density than the sponges, allowing easier identification of each MTS in the measurements. In other words, each filter is a solid marker indicating the position of at least one of the cell cultures (MTS) in the column.

Four different columns were introduced into the micro-PET scanner and scanned:
a) a column prepared with silk sponges without cell cultures (background measurement),
b) a column prepared with spheroids pre-incubated with [$^{18}$F] FDG (signal-to-noise ratio measurement),
c) a column prepared with spheroids which were placed in different distances and the [$^{18}$F] FDG was introduced in a stop-flow mechanism (see FIG. 5), and
d) a column prepared with cells grown on silk sponges with a cell-free sponge in between (see FIG. 6).

The scan of column a) showed low binding of [$^{18}$F] FDG to the silk sponge and low unspecific binding of polar compounds to silk in general.

The scan of column b) clearly indicated that the spheroids could be successfully detected within the column.

The scan of column c) confirmed the low specific binding of [$^{18}$F] FDG to the silk scaffold, and portrayed a surprisingly high resolution between the spheroids, as all spheroids could be imaged separately, except for the spheroids 2 and 3. This result is particularly important, as the spheroid size of approximately 700 µm lies below the resolution of the micro-PET device used.

The scan of column d) clearly highlights the regions with HT29 cells (see FIG. 6), further indicating the high potential of the present invention.

NON-PATENT REFERENCES

Carfi-Pavia, F. et al. Porous poly (L-lactic acid) scaffolds are optimal substrates for internal colonization by A6 mesoangioblasts and immunocytochemical analyses. J. Biosci. 34, 873-879 (2009).

Chatziioannou, Arion F. "Instrumentation for molecular imaging in preclinical research: Micro-PET and Micro-SPECT." Proceedings of the American Thoracic Society 2.6 (2005): 533-536.

Hirschhaeuser, Franziska, et al. "Multicellular tumor spheroids: an underestimated tool is catching up again." Journal of biotechnology 148.1 (2010): 3-15.

Keshari, Kayvan R., et al. "Metabolic response of prostate cancer to nicotinamide phophoribosyltransferase inhibition in a hyperpolarized MR/PET compatible bioreactor." The Prostate 75.14 (2015): 1601-1609.

Koba, Wade, Linda A. Jelicks, and Eugene J. Fine. "Micro-PET/SPECT/CT imaging of small animal models of disease." The American journal of pathology 182.2 (2013): 319-324.

Mizuno, Shuichi, et al. "Effects of physical stimulation on chondrogenesis in vitro." Materials Science and Engineering: C 6.4 (1998): 301-306.

Poonam, V., Vipin, V., Pratima, R. & R, R. A. Agar-gelatin hybrid sponge-induced three-dimensional in vitro 'liver-like' HepG2 spheroids for the evaluation of drug cytotoxicity. J. Tissue Eng. Regen. Med. 4, 524-531 (2010).

Rnjak-Kovacina, J. et al. Lyophilized Silk Sponges: A Versatile Biomaterial Platform for Soft Tissue Engineering. ACS Biomater. Sci. Eng. 1, 260-270 (2015).

Rohanizadeh, R., Swain, M. V. & Mason, R. S. Gelatin sponges as a scaffold for osteoblasts. J. Mater. Sci. Mater. Med. 19, 1173-1182 (2008).

Shapiro, L. & Cohen, S. Novel alginate sponges for cell culture and transplantation. Biomaterials 18, 583-590 (1997)

Teuschl, A. H., Zipperle, J., Huber-Gries, C. & Kaplan, D. L. Silk fibroin based carrier system for delivery of fibrinogen and thrombin as coagulant supplements. J. Biomed. Mater. Res.—Part A 105, 687-696 (2017).

Whitehead, Timothy D., et al. "Artificial tissue bioreactor (ATB) for biological and imaging applications." Engineering in Medicine and Biology Society (EMBC), 2012 Annual International Conference of the IEEE. IEEE, 2012.

Whitehead, Timothy D., et al. "A PET-compatible tissue bioreactor for research, discovery, and validation of imaging biomarkers and radiopharmaceuticals: system design and proof-of-concept studies." Journal of Nuclear Medicine 54.10 (2013): 1812-1819.

Widdowson, J. P., Picton, A. J., Vince, V., Wright, C. J. & Mearns-Spragg, A. In vivo comparison of jellyfish and bovine collagen sponges as prototype medical devices. J. Biomed. Mater. Res.—Part B Appl. Biomater. 1-10 (2017).

The invention claimed is:

1. A method for concurrent micro-positron emission tomography (micro-PET) or micro-single photon emission computed tomography (micro-SPECT) of at least two cell cultures in a biocompatible column,
    the column comprising an inlet, an axially oriented perfusion chamber and an outlet, wherein the inlet is fluidly connected to the perfusion chamber and the outlet is fluidly connected to the perfusion chamber, wherein the perfusion chamber comprises a porous solid phase, an aqueous liquid phase, a first cell culture and a second cell culture, wherein at least a portion of the first cell culture and at least a portion of the second cell culture are in contact with the solid phase and wherein the first cell culture is separated from the second cell culture by at least a portion of the solid phase;
    the method comprising the steps of:
        (A) inserting the column into a micro-PET or micro-SPECT scanner;
        (B) conducting an aqueous labelling liquid comprising a radioactive tracer via the inlet through the perfusion chamber towards the outlet, such that at least a portion of the cells of the first cell culture and at least a portion of the cells of the second cell culture are contacted with the radioactive tracer;
        (C) conducting an aqueous washing liquid via the inlet through the perfusion chamber towards the outlet, such that at least a portion of the radioactive tracer is removed from the perfusion chamber through the outlet; and
        (D) scanning the column with the micro-PET or micro-SPECT scanner.

2. The method of claim 1, wherein the first cell culture and/or the second cell culture is a spheroid or an organoid.

3. The method of claim 2, wherein the first cell culture and/or the second cell culture is a multicellular tumour spheroid (MTS).

4. The method of claim 1, wherein the conducting of step (B) and/or step (C) comprises turbulent liquid flow through the perfusion chamber, preferably with a flow rate of 0.01 ml/min to 10 ml/min, preferably 0.025 ml/min to 7.5 ml/min, more preferably 0.05 ml/min to 5 ml/min, especially 0.1 ml/min to 2 ml/min.

5. The method of claim 1, wherein the porous solid phase comprises at least one sponge comprising at least one biopolymer, preferably wherein the biopolymer is selected from silk, silk fibroin, collagen, gelatin, agarose, alginate, polylactic acid, agar, methyl-cellulose and mixtures thereof and/or wherein the sponge is pre-cut to fit into the perfusion chamber.

6. The method of claim 1, wherein the porous solid phase has an average pore diameter between 50 µm and 1000 µm, preferably between 75 µm and 750 µm, more preferably between 100 µm and 600 µm, even more preferably between 125 µm and 500 µm, yet even more preferably between 150 µm and 450 µm, especially between 200 µm and 400 µm.

7. The method of claim 1, wherein the minimal distance between the first cell culture and the second cell culture is at least 600 µm, preferably at least 700 µm, more preferably at least 800 µm, even more preferably at least 900 µm, yet even more preferably at least 1000 µm, especially at least 2000 µm or even at least 5000 µm.

8. The method of claim 5, wherein the porous solid phase comprises at least a first and a second of said sponges wherein at least a portion of the first culture is in contact with the first sponge and at least a portion of the second culture is in contact with the second sponge.

9. The method of claim 8, wherein the first sponge has a recess comprising at least a portion of the first cell culture and the second sponge has a recess comprising at least a portion of the second cell culture.

10. A biocompatible column for concurrent micro-PET or micro-SPECT of at least two cell cultures,
the column comprising: an inlet, an axially oriented perfusion chamber and an outlet, wherein the inlet is fluidly connected to the perfusion chamber and the outlet is fluidly connected to the perfusion chamber,
wherein the perfusion chamber comprises a porous solid phase comprising at least one sponge comprising at least one biopolymer, an aqueous liquid phase, a first cell culture and a second cell culture, wherein at least a portion of the first cell culture and at least a portion of the second cell culture are in contact with the solid phase and wherein the first cell culture is separated from the second cell culture by at least a portion of the solid phase.

11. The column of claim 10, wherein the biopolymer is silk fibroin.

12. A system for concurrent micro-PET or micro-SPECT of at least two cell cultures, comprising the column of claim 10 fluidly connected to a pump via the inlet and/or the outlet, preferably wherein the system further has a temperature control for the column and/or a sample injector fluidly connected to the inlet of the column.

13. A micro-PET or micro-SPECT scanner with the column of claim 10 inserted.

14. A kit for concurrent micro-PET or micro-SPECT of at least two cell cultures, comprising:
at least one biocompatible column for concurrent micro-PET or micro-SPECT of at least two cell cultures,
the column comprising an inlet, an axially oriented perfusion chamber and an outlet, wherein the inlet is fluidly connected to the perfusion chamber and the outlet is fluidly connected to the perfusion chamber; and
at least two sponges comprising at least one biopolymer, preferably selected from silk, silk fibroin, collagen, gelatin, agarose, alginate, polylactic acid, agar, methyl-cellulose and mixtures thereof, wherein the sponges are pre-cut to fit into the perfusion chamber.

15. The kit of claim 14, further comprising at least two filters pre-cut to fit into the perfusion chamber, preferably wherein the filters have a higher density than the at least two sponges, more preferably at least 1.25× as high, even more preferably at least 1.5× as high, especially at least 2× as high.

* * * * *